US012220300B2

(12) United States Patent
Edwards et al.

(10) Patent No.: US 12,220,300 B2
(45) Date of Patent: Feb. 11, 2025

(54) PARTIALLY TRANSPARENT WOUND DRESSING

(71) Applicant: Solventum Intellectual Properties Company, Maplewood, MN (US)

(72) Inventors: Thomas A. Edwards, Hampshire (GB); Christopher B. Locke, Bournemouth (GB); Timothy M. Robinson, Wimbourne (GB); Justin A. Long, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 661 days.

(21) Appl. No.: 17/424,009

(22) PCT Filed: Jan. 27, 2020

(86) PCT No.: PCT/US2020/015188
§ 371 (c)(1),
(2) Date: Jul. 19, 2021

(87) PCT Pub. No.: WO2020/159859
PCT Pub. Date: Aug. 6, 2020

(65) Prior Publication Data
US 2022/0079815 A1 Mar. 17, 2022

Related U.S. Application Data

(60) Provisional application No. 62/799,998, filed on Feb. 1, 2019.

(51) Int. Cl.
*A61F 13/0203* (2024.01)
*A61F 13/00* (2024.01)
(Continued)

(52) U.S. Cl.
CPC ...... *A61F 13/0223* (2013.01); *A61F 13/0206* (2013.01); *A61F 13/022* (2013.01); *A61F 13/0276* (2013.01); *A61F 2013/00182* (2013.01)

(58) Field of Classification Search
CPC ...... A61F 13/00; A61F 13/02; A61F 13/0203; A61F 13/0206; A61F 13/0209;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Chinese Office Action for Corresponding Application No. 2020800112852, mailed Jan. 12, 2022.
(Continued)

*Primary Examiner* — Alireza Nia
*Assistant Examiner* — Andrew Jun-Wai Mok

(57) ABSTRACT

A partially transparent dressing includes a fluid management core having a first side and a second, wound-facing side. The fluid management core includes an absorbent material and a plurality of optically transparent windows. The dressing includes a barrier layer coupled to the first side and a patient interface layer coupled to the second side. A fluid communication port is disposed in the second side. An opening is disposed in the patient interface layer. The opening is configured to receive fluid from a wound.

23 Claims, 8 Drawing Sheets

(51) Int. Cl.
*A61F 13/02* (2024.01)
*A61F 13/0206* (2024.01)

(58) Field of Classification Search
CPC .............. A61F 13/022; A61F 13/0223; A61F 13/0226; A61F 13/0243; A61F 13/0246; A61F 13/0253; A61F 13/0256; A61F 13/0266; A61F 2013/00246; A61F 2013/00251; A61F 2013/00255; A61L 31/146; A61M 1/90; A61M 1/91; A61M 1/98; A61M 1/912–913; A61M 1/915–918
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0173434 A1* | 8/2006 | Zoromski | A61F 13/53 604/374 |
| 2010/0030170 A1* | 2/2010 | Keller | A61F 13/8405 604/360 |
| 2016/0144084 A1* | 5/2016 | Collinson | A61F 13/05 604/319 |

FOREIGN PATENT DOCUMENTS

| | | | |
|---|---|---|---|
| AU | 755496 B2 | 12/2002 | |
| CA | 2005436 A1 | 6/1990 | |
| CN | 106659590 A | 5/2017 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2412589 A * | 10/2005 | ............. A61F 13/00 |
| GB | 2527617 A * | 12/2015 | ....... A61F 13/00008 |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |

(56) References Cited

FOREIGN PATENT DOCUMENTS

| WO | 97/18007 A1 | 5/1997 | | |
|---|---|---|---|---|
| WO | 99/13793 A1 | 3/1999 | | |
| WO | WO-2005/079718 A1 | 9/2005 | | |
| WO | WO-2012125530 A1 * | 9/2012 | ......... | A61F 13/0246 |
| WO | WO-2014/020443 A2 | 2/2014 | | |
| WO | WO-2015193257 A1 * | 12/2015 | ....... | A61F 13/00008 |

OTHER PUBLICATIONS

International Search Report and Written Opinion on International Patent Application No. PCT/US2020/015188 dated Apr. 23, 2020 (9 pages).
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoviƈ?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

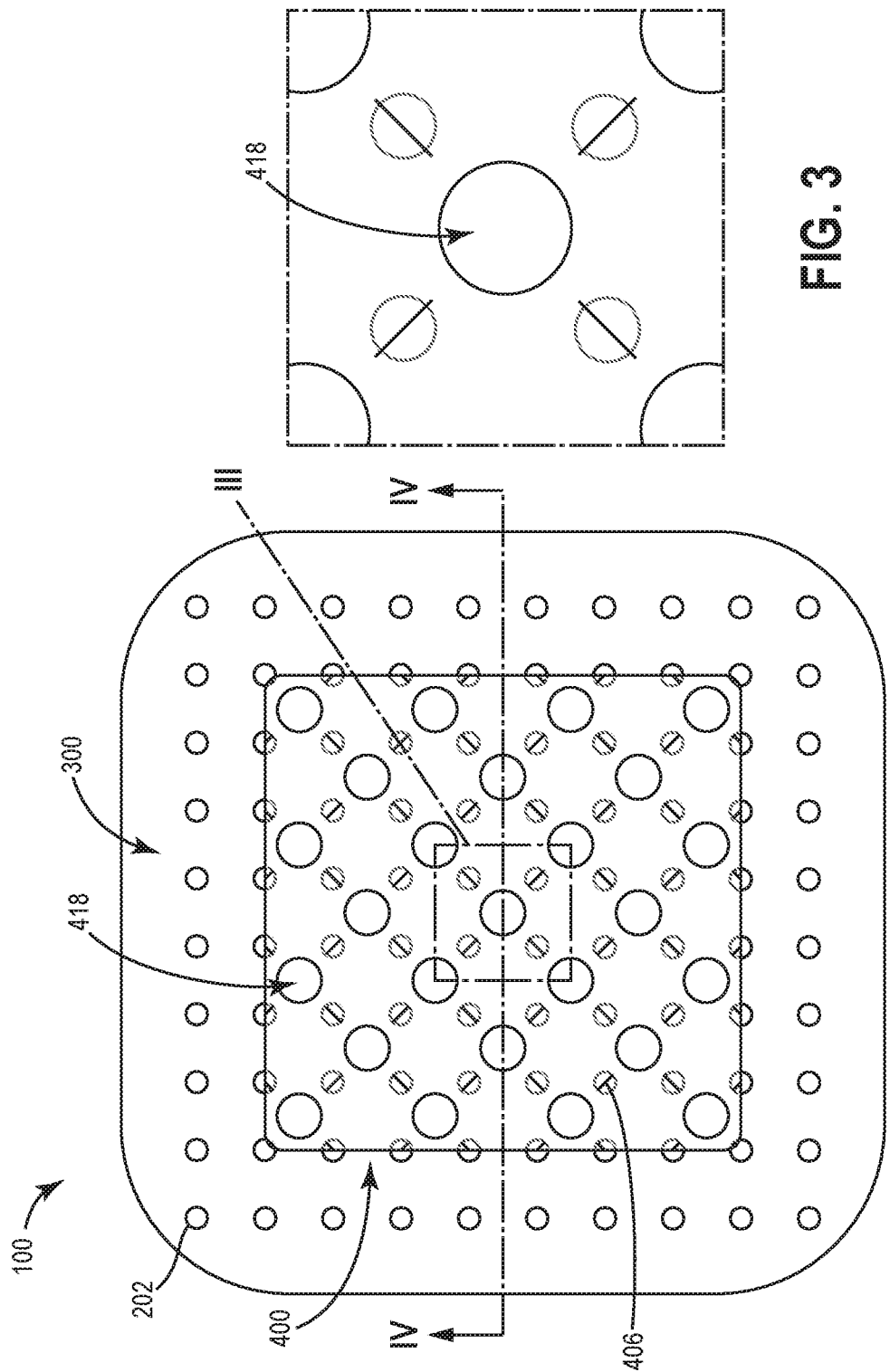

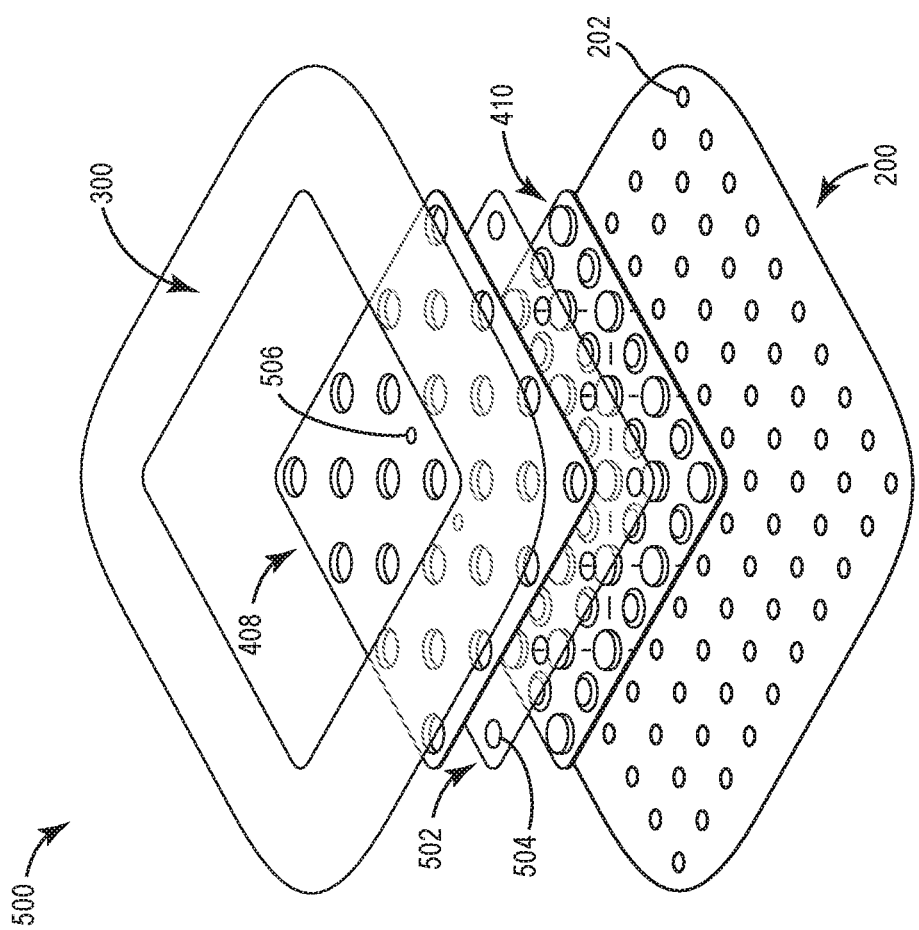

PARTIALLY TRANSPARENT WOUND DRESSING

CROSS-REFERENCE TO RELATED APPLICATIONS

This application is a US national phase application under 35 USC § 371 of International Application No. PCT/US2020/015188 filed on Jan. 27, 2020, which claims the benefit of priority to U.S. Provisional Application No. 62/799,998, entitled "PARTIALLY TRANSPARENT WOUND DRESSING" filed on Feb. 1, 2019, which are both hereby incorporated herein by reference in its their entireties.

BACKGROUND

The present disclosure relates generally to wound dressings. More specifically, the present disclosure relates to a partially transparent wound dressing.

In many instances, the condition of a wound can be determined through visual assessment by a caregiver or trained clinician. The condition of the wound may be determined, in part, by the color and surface texture of the wound along with the amount of discharge present at the wound site. These features assist caregivers in distinguishing between healthy wound beds and old or infected wound beds.

In order to visually assess the wound site, a caregiver must first remove the dressing from the wound site. Conventional wound dressings are opaque and include materials that become discolored during use, preventing the caregiver from visually inspecting the wound site. The periodic examination and redressing of the wound may cause patient discomfort and distress. Additionally, in many cases the dressing is removed before it is fully saturated, leading to waste and increasing the cost of care.

SUMMARY

One implementation of the present disclosure is a dressing. The dressing includes a fluid management core having a first side and a second, wound-facing side. The fluid management core includes an absorbent material and a plurality of windows. The second side includes a fluid communication port. The dressing also includes a barrier layer and a patient interface layer. The barrier layer is coupled to the first side of the fluid management core. The patient interface layer is coupled to the second side of the fluid management core. The patient interface layer includes an opening configured to receive fluid from a wound.

In any of the above embodiments, each window of the plurality of windows may be configured to provide partial visibility through the fluid management core.

In some embodiments, the fluid management core includes a first fluid management layer and a second fluid management layer. The absorbent material may be sandwiched between the first fluid management layer and the second fluid management layer.

In some embodiments, the first fluid management layer includes a first plurality of extensions extending toward the second fluid management layer. The second fluid management layer may be coupled to the first plurality of extensions. The plurality of extensions may include a plurality of geodesic structures. In some embodiments, the second fluid management layer may include a second plurality of extensions aligned with the first plurality of extensions. The first plurality of extensions may be coupled to the second plurality of extensions.

In any of the above embodiments, the first fluid management layer and the second fluid management layer may be substantially identical.

In any of the above embodiments, each window of the plurality of windows may have a diameter within a range between approximately 3 mm and 15 mm.

In any of the above embodiments, the fluid communication port may include a fenestration configured to receive fluid from the opening in the patient interface layer.

In any of the above embodiments, the barrier layer may include an aperture. The aperture may be substantially centered over the first fluid management layer.

In any of the above embodiments, the fluid management core may be centered over the patient interface layer. The barrier layer may be coupled to the patient interface layer.

In some embodiments, the dressing includes a wicking layer sandwiched between the fluid management core and the patient interface layer. The wicking layer may include a plurality of perforations that are substantially aligned with the windows.

In some embodiments, the dressing includes a fluid removal port disposed in the first side of the fluid management core. The fluid removal port may be configured to allow fluid to be removed from the fluid management core.

Another implementation is a dressing. The dressing includes a barrier layer, a first fluid management layer, and a second fluid management layer. The first fluid management layer is coupled to the barrier layer. The first fluid management layer includes a first plurality of extensions. The second fluid management layer is coupled to a first plurality of extensions. One of the fluid management layers includes a fluid communication port. The dressing also includes an absorbent layer disposed in a cavity between the first fluid management layer and the second fluid management layer. The dressing further includes a patient interface layer coupled to one of the fluid management layers. The patient interface layer includes an opening that is at least partially aligned with the fluid communication port.

In some embodiments, the first plurality of extensions includes a plurality of geodesic structures.

In some embodiments, the second fluid management layer includes a second plurality of extensions coupled to the first plurality of extensions. The first fluid management layer and the second fluid management layer may be substantially identical except for the fluid communication port.

In some embodiments, a contact area between each extension of the first plurality of extensions and the second fluid management layer forms a window having a diameter within a range between approximately 3 mm and 15 mm.

In some embodiments, the dressing further includes a wicking layer sandwiched between the patient interface layer and one of the fluid management layers. The wicking layer may include a plurality of perforations substantially aligned with the first plurality of extensions.

In some embodiments, the dressing further includes a fluid removal port disposed in one of the fluid management layers. The fluid removal port may be configured to allow fluid to be removed from the absorbent layer.

Another implementation of the present disclosure is a method of making a dressing. The method includes providing a barrier layer, providing a first fluid management layer having a first plurality of extensions, providing an absorbent layer, providing a second fluid management layer having a fluid communication port, and providing a patient interface layer having an opening. The method includes placing the absorbent layer onto one of the fluid management layers and joining the fluid management layers to form a fluid management core. The method also includes placing the fluid management core onto the patient interface layer. The method further includes placing the barrier layer onto the fluid management core opposite the patient interface layer.

In some embodiments, the method includes aligning a first plurality of extensions on the first fluid management core with a second plurality of extensions on the second fluid management core.

In some embodiments, the method includes aligning the opening with the fluid communication port.

In some embodiments, the method includes printing the absorbent layer onto one of the fluid management layers.

In some embodiments, the method includes bonding the fluid management core to the patient interface layer and the barrier layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIG. 2 is a top view of a dressing, according to an exemplary embodiment;

FIG. 3 is a top view of a central region of a wound dressing, according to an exemplary embodiment;

FIG. 7 is an exploded view of a dressing, according to another exemplary embodiment;

DETAILED DESCRIPTION

Overview

Referring generally to the FIGURES, a partially transparent dressing is provided that allows a caregiver to view a wound site without having to remove and replace the dressing. The dressing includes a patient interface layer, a barrier layer, and a fluid management core. The fluid management core is "sandwiched" or otherwise disposed between the patient interface layer and the barrier layer. The fluid management core includes a plurality of windows through which the wound site may be visually examined. According to an exemplary embodiment, the fluid management core includes a first fluid management layer and a second fluid management layer. The first fluid management layer is coupled to the second fluid management layer. The fluid management layers are spaced apart from one another by a plurality of extensions. The extensions may be formed into one or both of the fluid management layers. The extensions may include cylindrical depressions or another geodesic structure formed into the fluid management layers. A contact area between each pair of extensions, or between each extension and the first or second fluid management layer, forms an optically transparent window through which the wound bed can be observed.

The fluid management core includes an absorbent material deposited in a cavity between the fluid management layers. The absorbent material is configured to absorb and remove wound exudate from the wound site. Fluids are received from the wound site through a fluid communication port disposed in the second side of the fluid management core. The fluid communication port is substantially aligned with an opening in the patient interface layer. The space in between the fluid management layers provides room for the absorbent material to expand as fluid enters the dressing. The extensions provide pressure relieving benefits to the dressing, preventing significant structural deformation or collapse of the fluid management core under compression, helping to retain fluid in the absorbent layer, and reducing the risk of maceration associated with fluid retention at the wound site.

By providing continuous visual access to the wound site, the dressing allows a caregiver to identify potential risks and signs of poor wound health at a much earlier stage of progression, while limiting the amount of patient trauma associated with wound redressing. These and other features and advantages of the dressing are described in detail below.

Dressing Construction

Figure 1:
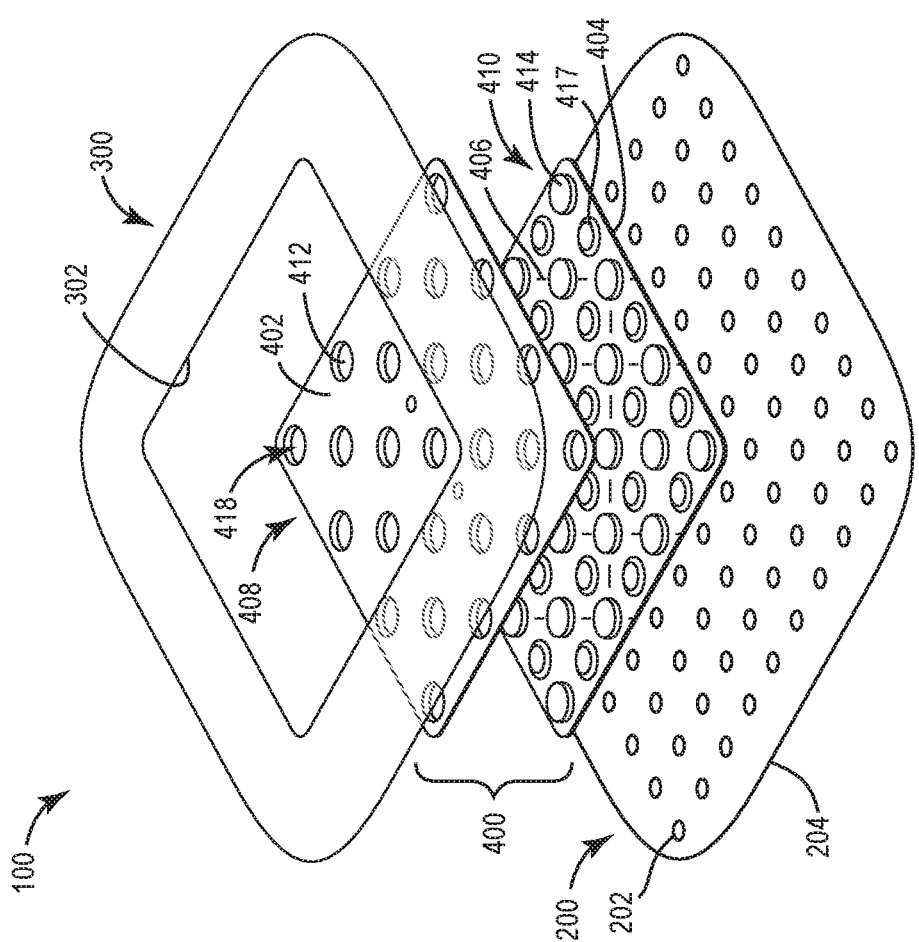
FIG. 1 is an exploded view of a dressing, according to an exemplary embodiment.

FIG. 1 provides an optically transparent dressing, shown as dressing 100, according to an exemplary embodiment. The dressing 100 is configured to provide visual access to a wound site throughout the duration of treatment. The dressing 100 includes a patient interface layer 200, a barrier layer 300, and a fluid management core 400. The fluid management core 400 is sandwiched between the patient interface layer 200 and the barrier layer 300. The fluid management core 400 is centered over the patient interface layer 200. The fluid management core 400 includes a first side 402 and a second, wound-facing side, shown as second side 404. As shown in FIG. 1, the first side 402 of the fluid management core 400 is coupled to the barrier layer 300. The second side 404 of the fluid management core 400 is coupled to the patient interface layer 200. The dressing 100 includes a plurality of fluid communication ports 406 disposed in the second side 404 of the fluid management core 400. Each of the fluid communication ports 406 is configured to receive fluid (e.g., wound exudate) from a wound site.

Fluid passing through the plurality of fluid communication ports 406 is received within a cavity defined by two opposing members of the fluid management core 400. The opposing members include a first fluid management layer 408 and second fluid management layer 410. As shown in FIG. 1, the first fluid management layer 408 includes a first plurality of extensions 412 oriented substantially normal to the first fluid management layer 408. The first plurality of extensions 412 include substantially cylindrical depressions in the first fluid management layer 408. The extensions 412 extend from an inner surface of the first fluid management layer 408 toward the second fluid management layer 410. According to an exemplary embodiment, the second fluid management layer 410 is substantially similar to the first fluid management layer 408. The second fluid management layer 410 includes a second plurality of extensions 414, each one of the second plurality of extensions 414 aligned with a corresponding one of the first plurality of extensions 412.

As shown in FIG. 1, the fluid management core 400 includes an absorbent layer 417 configured to absorb and remove wound exudate from a wound (e.g., a wound bed, a wound site, etc.). The absorbent layer 417 is coupled to at least one of the fluid management layers 408, 410. The absorbent layer 417 is deposited interstitially between adjacent ones of the second plurality of extensions 414.

As shown in FIG. 1, the patient interface layer 200 includes a plurality of openings 202, each opening 202 aligned with a corresponding one of the fluid communication ports 406 in the fluid management core 400. Referring to FIGS. 2-3, a top view of the dressing 100 is shown, according to an exemplary embodiment. As shown in FIGS. 2-3, the fluid communication ports 406 include fenestrations (e.g., substantially linear slits or cuts, etc.) disposed midway between adjacent pairs of extensions 414 on the second fluid management layer 410. The spacing between fenestrations is substantially the same as the spacing between openings 202 in the patient interface layer 200. The openings 202 are configured to fluidly couple the fluid management core 400 to the wound bed. Fluid passing through the openings 202 is received in a cavity (e.g., fluid pathway, etc.) formed between the fluid management layers 408, 410.

The fluid management core 400 is formed by a layered arrangement of the first fluid management layer 408, the absorbent layer 417, and the second fluid management layer 410. As shown in FIG. 2, each one of the first plurality of extensions 412 is configured to engage with a corresponding one of the second plurality of extensions 414. According to an exemplary embodiment, the first plurality of extensions 412 is coupled to the second plurality of extensions 414. The surfaces of the extensions 412, 414 (e.g., outer surfaces, surfaces oriented substantially parallel to the fluid management layers 408, 410, etc.) may be pretreated with a transparent adhesive prior to joining the fluid management layers 408, 410. Alternatively, the surfaces may be coupled via welding, heat bonding, or another suitable joining process. Once coupled, a contact area between each one of the first plurality of extensions 412 and each one of the second plurality of extensions 414 forms an optically transparent (or translucent) window 418. The number of windows 418 is approximately equal to the number of extensions 412, 414. As shown in FIG. 3, a diameter of each window 418 is approximately equal to a diameter of a circular depression defining the surface of each extension 412, 414. In some embodiments, the diameter of each window 418 may vary within a range between 3 mm and 15 mm. In alternative embodiments, the number, shape, size, and arrangement of windows 418 may be different.

Figure 4:
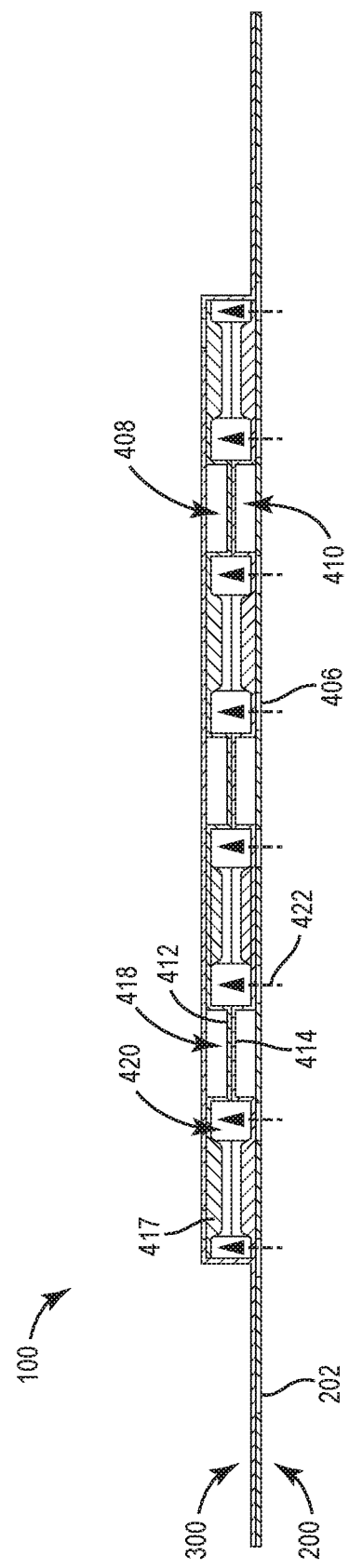
FIG. 4 is a sectional view of a wound dressing, according to an exemplary embodiment.

Referring now to FIG. 4, a side view of the dressing 100 is shown, at a cross-section through a row of extensions 412, 414, according to an exemplary embodiment. Together, the fluid management layers 408, 410 define a cavity 420 (e.g., a fluid pathway, etc.) configured to receive fluid from the wound site. Dashed arrows 422 indicate the flow direction of wound exudate entering the fluid management core 400. As shown in FIG. 4, an outer, wound-facing side, shown as outer surface 204 of the patient interface layer 200 is configured to be placed in contact with a wound bed. Fluid from the wound bed passes through the openings 202 in the patient interface layer 200 and the fluid communication ports 406 on the second side 404 of the fluid management core 400 (e.g., fenestrations in the second fluid management layer 410). Fluid entering the cavity 420 is absorbed by the absorbent layer 417, which expands to fill the cavity 420.

The bond (e.g., joint, connection, etc.) between the extensions 412, 414 prevents fluid from blocking the windows 418. As shown in FIG. 4, the bond (e.g., joint, connection, etc.) between the second side 404 of the fluid management core 400 and the patient interface layer 200 prevents fluid from entering depressed areas 421 on the second side 404 of the fluid management core 400 (e.g., hollow spaces defined by each one of the second plurality of extensions 414).

Referring to FIGS. 1-2, the barrier layer 300 is configured as a barrier film to protect both the wound site and any external surfaces from contamination. The barrier layer 300 includes an aperture 302 disposed centrally on the barrier layer 300. The aperture 302 is substantially centered over the fluid management core 400. The barrier layer 300 engages with the fluid management core 400 proximate to a perimeter of the first fluid management layer 408. The barrier layer 300 also engages with an outer portion of the patient interface layer 200 (e.g., a portion of the patient interface layer 200 that extends outward from the perimeter of the second fluid management layer 410). The barrier layer 300 substantially covers the openings 202 in the outer portion of the patient interface layer 200 so as to prevent fluid from leaking out from the edges of the dressing 100 and protect the wound site and tissue surrounding the wound. The outer dimensions of the barrier layer 300 are identical or substantially similar to the outer dimensions of the patient interface layer 200.

The combination of features shown in the exemplary embodiment of FIGS. 1-4 should not be considered limiting. Many alternative implementations are possible without departing from the inventive concepts disclosed herein. For example, in some embodiments, the extensions may be formed into only one of the first fluid management layer and the second fluid management layer. The extensions may engage with an inner surface of the opposing fluid management layer, rather than an opposing set of extensions. The windows may be formed within a region of contact (e.g., a contact area, etc.) between the extensions and the inner surface. Additionally, the number, shape, size, and/or arrangement of extensions may be different in various alternative embodiments.

First Fluid Management Layer

Figure 5:
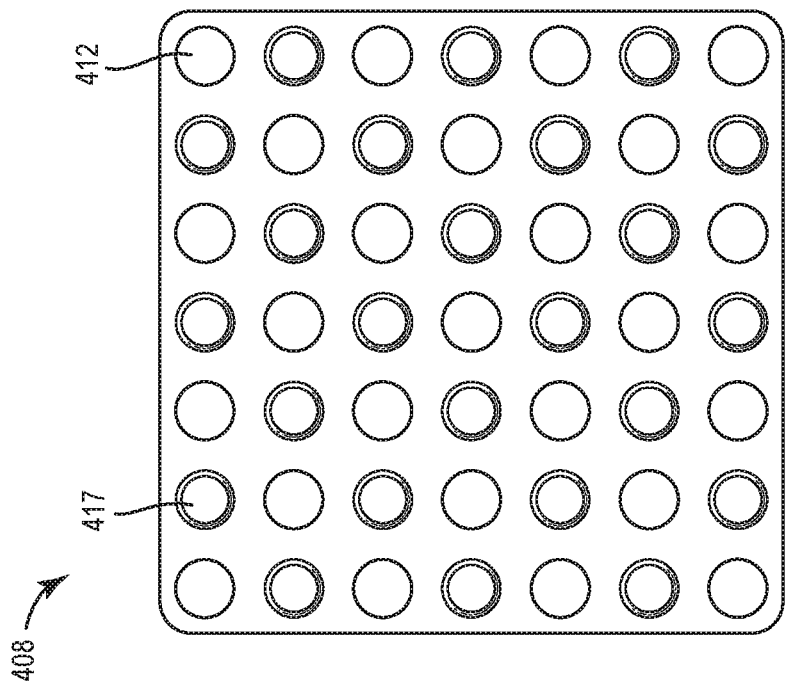
FIG. 5 is a top view of a first fluid management layer, according to an exemplary embodiment.

FIG. 5 provides a fluid management layer, shown as first fluid management layer 408, according to an exemplary embodiment. As shown in FIG. 1, the first fluid management layer 408 is configured as an upper fluid management layer for a fluid management core 400. The first fluid management layer 408 may be made from a thermoplastic polyurethane (TPU) film, such as Vacive 3 mil polyurethane, or another formable and optically transparent material. The first fluid management layer 408 includes a first plurality of extensions 414. The first plurality of extensions 414 may be thermoformed or otherwise formed into the first fluid management layer 408. The first plurality of extensions 414 may be formed in a variety of different shapes, for example, cylinders, domes, triangular depressions, or another geodesic shape. As shown in FIG. 5, each one of the first plurality of extensions 414 is substantially cylindrical. The extensions 414 provide structural support to the fluid management core 400 and help to prevent the cavity 420 from collapsing when external pressure is applied to the dressing 100. The extensions 414 also help to reposition the fluid management layers 408, 410 after the pressure is removed from the dressing 100. A size of each individual extension 414 (e.g., a diameter of a planar surface of each extension 414, a cross-sectional area of a planar surface of each extension 414, etc.) or a number of extensions 414 may be modified as needed to balance visual access to the wound site with fluid retention and structural support against compressive loading (e.g., pressure relieving benefits).

In some embodiments, the first fluid management layer 408 is configured to allow fluid to evaporate into the surroundings. The material thickness and type may be selected based on a target moisture vapor transmission rate (MVTR), which maximizes the healing benefits of the dressing 100. For example, the MVTR may be within a range between 250 g/m²/day to 400 g/m²/day or greater. In some embodiments, the MVTR may increase as part of the thermoforming process.

Second Fluid Management Layer

Figure 6:
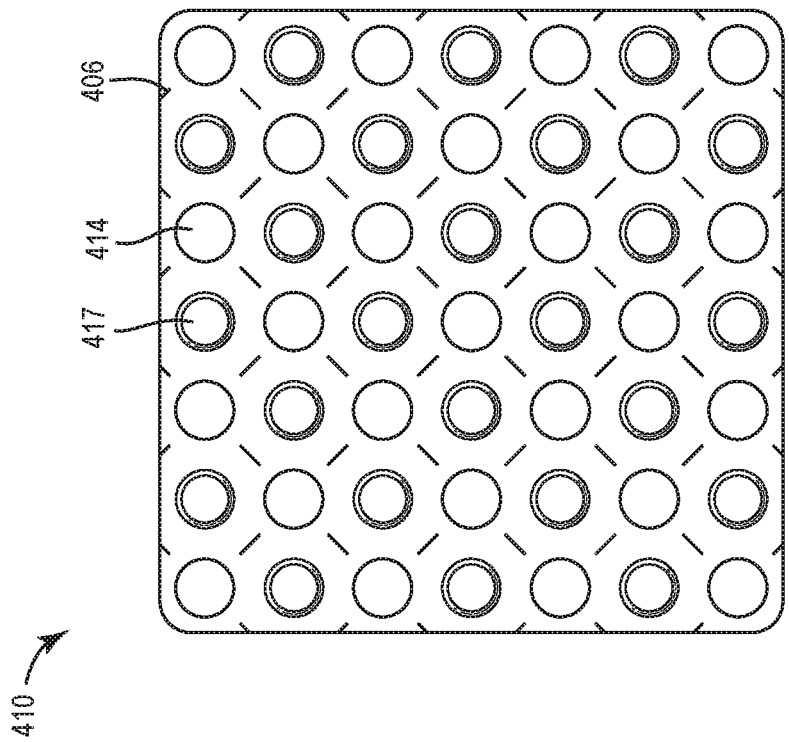
FIG. 6 is a top view of a lower fluid management layer, according to an exemplary embodiment.

FIG. 6 provides another fluid management layer, shown as second fluid management layer 410. As shown in FIG. 1, the second fluid management layer 410 is configured as a lower, wound-facing fluid management layer for the fluid management core 400. The second fluid management layer 410 includes a second plurality of extensions 414. Referring again to FIG. 6, the second fluid management layer 410 is substantially identical (e.g., similar) to the first fluid management layer 408, including the size, shape, number, and arrangement of extensions 414.

As shown in FIG. 6, the second fluid management layer 410 includes a plurality of fluid communication ports 406 extending through the fluid management layer 410, from a first side of the fluid management layer 410 to a second, wound-facing side of the fluid management layer 410. The fluid communication ports 406 are configured to fluidly couple a cavity 420 between the fluid management layers 408, 410 to openings 202 in the patient interface layer 200 (see also FIG. 1). According to an exemplary embodiment, the fluid communication ports 406 include fenestrations configured to receive fluid from the openings 202 in the patient interface layer 200. As shown in FIG. 6, the fluid communication ports 406 are disposed between adjacent pairs of extensions 414 so as to more fully expose the cavity 420 to fluid from the wound bed.

Absorbent Layer

As shown in FIGS. 5-6, the dressing 100 includes an absorbent layer 417 configured to absorb wound exudate and remove it from the wound bed. According to an exemplary embodiment, the absorbent layer 417 includes a superabsorbent polymer (SAP). In some embodiments, the absorbent layer 417 includes a plurality of nodules, dots, bumps, lumps, islands, protuberances, or other suitable form of deposition.

In some embodiments, absorbent layer 417 may be formed from or otherwise include a superabsorbent polymer in the form of granules. The superabsorbent polymer may include Luquasorb 1160 or 1161, such as may be commercially available from BASF. The granules may be contained in a water-soluble carrier polymer. One example of the water-soluble carrier polymer is polyvinylpyrrolidone (PVP). The superabsorbent polymer and the water-soluble polymer may be formed into a slurry or a suspension using an organic solvent. The organic solvent may include propanone or propanol and may aid in delivery of the absorbent layer 417 to a side of the of the fluid management layers 408, 410. In some embodiments, to increase the softness of the superabsorbent granules, a plasticizer may be added to the slurry. In one embodiment, the plasticizer may be water. In some embodiments, the slurry to form the absorbent layer 417 may have a formulation of 20 parts by mass of PVP, 10 parts by mass of a superabsorbent polymer, 1 part by mass of glycerol, and 100 parts by mass of propanone. In some embodiments, to plasticize the granules, 1 part to 2 parts by mass of water may be added to the slurry mixture. In other embodiments, a water-soluble polymer superabsorbent precursor, such as acrylic acid or 2-acrylamido-2-methyl-propanesulfonic acid (AMPS), with suitable UV curing additives, may replace the superabsorbent polymer. Such a precursor may be a relatively low viscosity solution and can be printed onto the fluid management layers 408, 410 and exposed to UV light to form a soft gel, eliminating the need for a plasticizer. In some embodiments, the water-soluble polymer superabsorbent precursor may be similar to that used for preparing hydrogel coatings.

The slurry mixture is applied to one side of fluid management layers 408, 410 to form the absorbent layer 417. In some embodiments, the slurry may be applied to the fluid management layers 408, 410 through standard printing methods, such as silk screen printing, gravure printing, or by x-y plotter printing. The absorbent layer 417 may be in any non-contiguous shapes such as circles, squares, hexagons, hoops/halos, stars, crosses, a range of lines, or any combination of shapes disposed about the cylindrical protrusions. The absorbent layer 417 may be printed such it is substantially evenly distributed on the fluid management layers 408, 410 in between the extensions 412, 414. In other embodiments, the absorbent layer 417 may be printed in an uneven (e.g. non-uniform, random, etc.) pattern on the fluid management layers 408, 410. In some embodiments, the absorbent layer 417 may include a flexible plasticized hydrophilic polymer matrix having a substantially continuous internal structure. The absorbent layer 417 may be configured to swell upon absorption of fluid, such as wound fluid exudate, and expand within the space between the fluid management layers 408, 410.

As shown in FIGS. 5-6, the absorbent layer 417 is deposited onto the first fluid management layer 408 and second fluid management layer 410. In some embodiments, the absorbent layer 417 is only deposited on the second fluid management layer 410. The absorbent layer 417 is printed in a regular pattern (e.g., an ordered pattern) and spaced approximately equally across an inner surface of the fluid management layers 408, 410. As shown in FIGS. 5-6, the absorbent layer 417 includes a plurality of substantially cylindrical protrusions extending from the inner surface of the fluid management layers 408, 410. Each one of the cylindrical protrusions is disposed approximately mid-way between adjacent pairs of extensions 412, 414 on the fluid management layers 408, 410. In alternative embodiments, the shape, quantity, and distribution of the absorbent layer 417 may be different. In some embodiments, the absorbent layer 417 is printed or otherwise formed as a perforated sheet, where the perforations are sized to accommodate the extensions 412, 414 on either layer, so as to occupy a greater portion of the cavity 420.

Patient Interface Layer

Referring to FIGS. 1 and 4, the patient interface layer 200 is configured to engage with a wound bed. The patient interface layer 200 includes an inner surface, and an outer, wound-facing surface. The inner surface is coupled to the fluid management core 400. The outer surface is coupled to the wound bed. The patient interface layer 200 may be made from a polymer film (e.g., polyurethane film) or a medical textile (e.g., Asahi nylon). The patient interface layer 200 may include a suitable low tack adhesive (e.g., silicone or polyurethane gel) to facilitate bonding with the skin surrounding the wound. The adhesive may be applied to the outer surface of the patient interface layer 200 proximate to a perimeter of the patient interface layer 200, or at any other suitable location along the outer surface. In some embodiments, the adhesive may be distributed evenly across the outer surface.

As shown in FIG. 2, the patient interface layer 200 extends laterally beyond an outer perimeter of the fluid management core 400. In alternative embodiments, the patient interface layer 200 may be substantially the same size and shape as the fluid management core 400 (as the second fluid management layer 410, etc.). As shown in FIG. 2, the patient interface layer 200 includes a plurality of openings 202 configured to receive fluid from a wound. The openings 202 include substantially circular holes disposed in a regular pattern across the patient interface layer 200. The size, shape, number, and arrangement of holes may be different in various alternative embodiments.

Barrier Layer

Referring to FIG. 1, the barrier layer 300 is configured to protect both the wound bed and any external surfaces from contamination. The barrier layer 300 may be made from a thin high MVTR adhesive coated polyurethane film such as Inspire 2327/2317. The barrier layer 300 may be fully coated in adhesive. Alternatively, the barrier layer 300 may be pattern coated with adhesive so as to increase the MVTR of the dressing 100 (e.g., to improve breathability, to improve the healing effect provided by the dressing 100, etc.). According to an exemplary embodiment, the barrier layer 300 includes an aperture 302 disposed centrally on the barrier layer 300. As shown in FIG. 1, the aperture 302 is substantially rectangular (e.g., substantially similar to the shape of the fluid management core 400). A width of the aperture 302 is slightly less than a width of the fluid management core 400. A length of the aperture 302 is slightly less than a length of the fluid management core 400. Among other benefits, the aperture 302 helps to ensure maximum visibility through the windows 418 in the fluid management core 400.

Additional Layers and Configurations

FIG. 7 provides a dressing 500 including a wicking layer 502 (e.g., a wicking scrim layer, etc.), according to an exemplary embodiment. The wicking layer 502 is configured to distribute fluid evenly throughout a cavity (e.g., fluid pathway, etc.) between the first and second fluid management layers. The wicking layer 502 includes a plurality of perforations 504. The perforations may be formed 504 via die cutting operation or another suitable forming operation. A shape of the perforations 504 may be substantially similar to a cross-sectional shape of the extensions. The perforations 504 may be alignable with the extensions. In some embodiments, the wicking layer includes depressions configured to receive the absorbent layer. In yet other embodiments, the wicking layer includes multiple layers configured to receive an absorbent layer therebetween.

Figure 8:
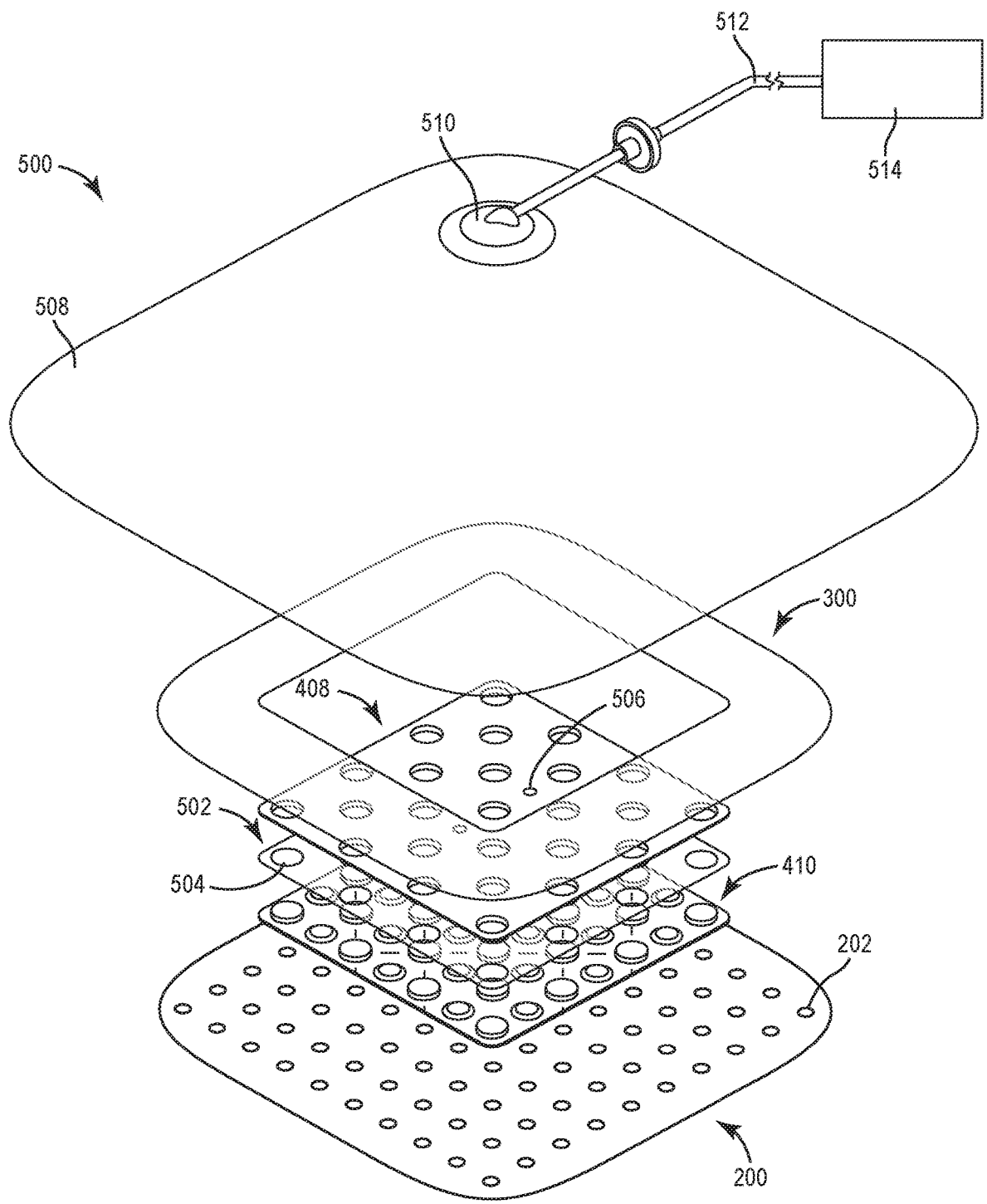
FIG. 8 is an exploded view of a dressing including a negative pressure wound therapy system, according to an exemplary embodiment.
Figure 9:
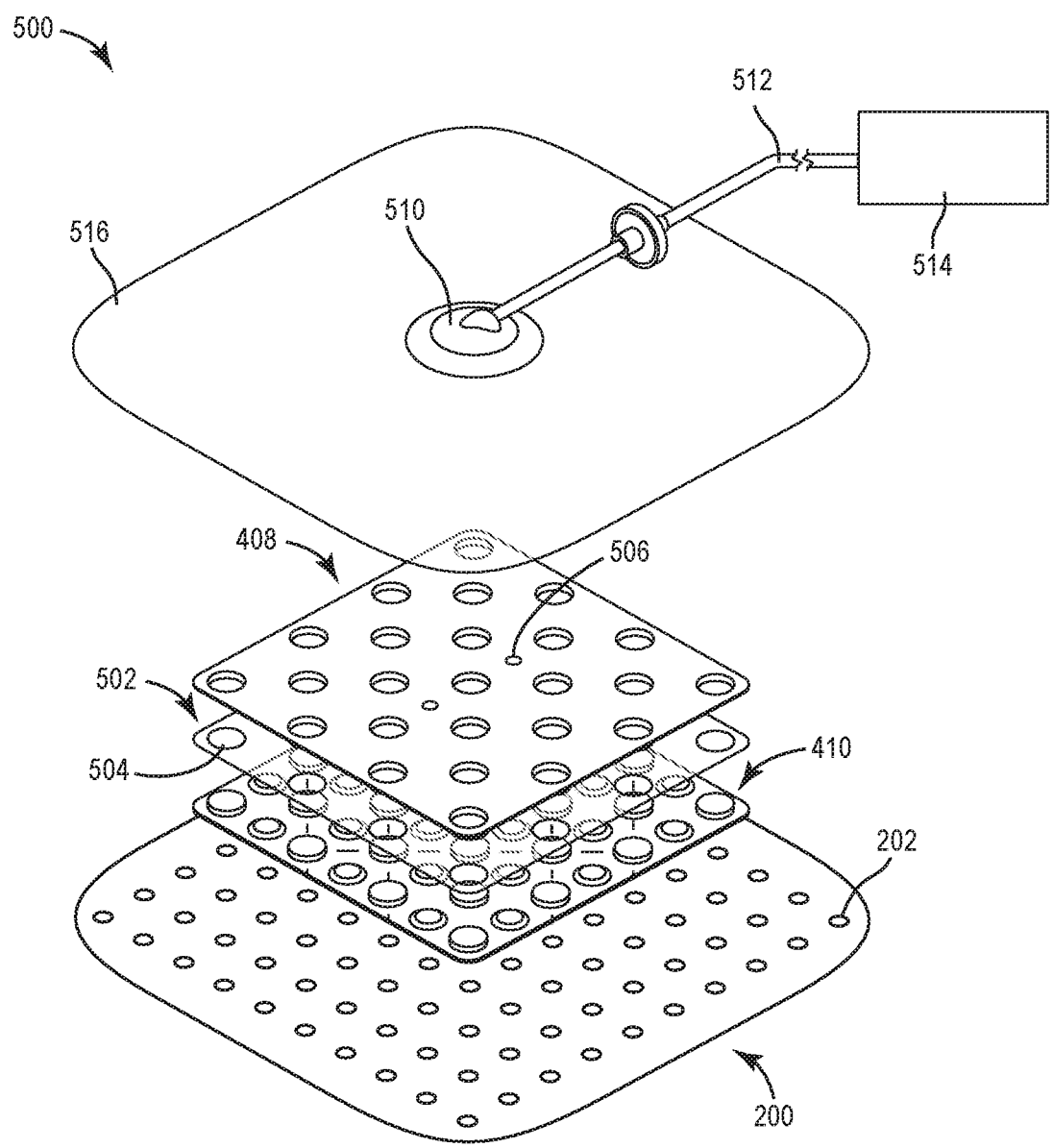
FIG. 9 is an exploded view of a dressing including a negative pressure wound therapy system, according to another exemplary embodiment.

As shown in FIG. 7, the dressing 500 additionally includes a fluid removal port 506 disposed in the first side of the fluid management core. The fluid removal port 506 is configured to allow fluid to be removed from the fluid management core. The fluid removal port 506 may be fluidly coupled to a negative pressure wound therapy system as shown in FIG. 8, which may, advantageously, increase the healing benefits provided by the dressing 500. The system may include a drape 508 coupled to the first side of the fluid management core, a hydrophobic filter 510, a tube set 512, and a negative pressure pump 514. In alternative embodiments, as shown in FIG. 9, the barrier layer 516 may be reconfigured to function as a drape; for example, by removing the aperture from the barrier layer 516 such that the barrier layer 516 substantially covers the fluid management core. Using the barrier layer 516 as the drape would reduce the overall complexity of the dressing. In some embodiments, the fluid removal port 506 includes a plurality of openings such as slots, slits, holes, etc. in the first side of the fluid management core. In some embodiments, the fluid removal port 506 is substantially similar to the fluid communication ports in the second fluid management layer.

In some embodiments, the negative pressure wound therapy system includes a canister configured to receive and store fluids from the wound bed. Advantageously, the canister eliminates the need for the hydrophobic filter 510 and the absorbent layer in the fluid management core, thereby reducing the number of layers that might otherwise obscure the view of the wound bed.

In some embodiments, the dressing 500 may additionally include an osmotic layer configured to filter the wound exudate before the fluid reaches the absorbent layer (e.g., to remove particulate from the wound exudate, etc.). Fluid received by the absorbent layer would be substantially clear/transparent and would allow the caregiver greater window of clarity across the dressing 500. The osmostic layer may be disposed in between the absorbent layer and the wound site to prevent any discoloration of the absorbent layer.

Method of Making a Wound Dressing

Figure 10:
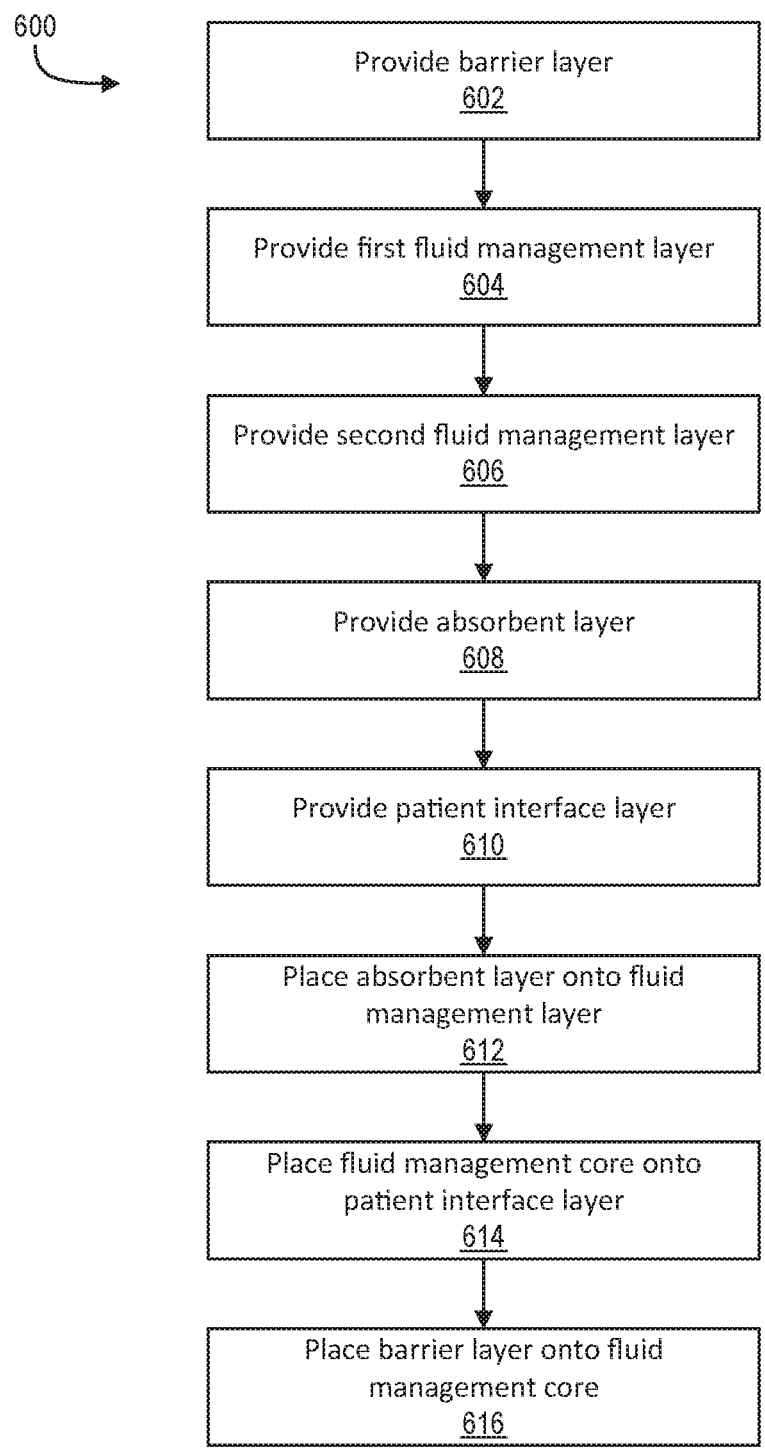
FIG. 10 is a block diagram of a method of making a dressing, according to an exemplary embodiment.

Referring now to FIG. 10, a method 600 of making a dressing is shown, according to an exemplary embodiment. The method 600 includes providing a barrier layer 602, providing a first fluid management layer 604, providing a second fluid management layer 606, providing an absorbent layer 608, and providing a patient interface layer 610. The first fluid management layer may include a first plurality of extensions. The second fluid management layer may include a second plurality of extensions. At least one of the fluid management layers may include a fluid communication point. The fluid communication point may be configured to receive fluid from an opening in the patient interface layer.

The layers may be joined (e.g., connected, etc.) prior to applying the dressing to a wound site. The method 600 includes placing the absorbent layer onto one of the fluid management layers 612. Operation 612 may include depositing an SAP onto the second fluid management layer. The SAP may be deposited onto the same side of the second fluid management layer as the extensions. The SAP may be deposited in between the extensions. Operation 612 may also include depositing an SAP onto the first fluid management layer. As shown in FIG. 10, the method also includes joining (e.g., connecting, coupling, etc.) the first fluid management layer and the second fluid management layer 612 so as to form a fluid management core. Operation 612 may include aligning the first plurality of extensions with the second plurality of extensions. Alternatively, operation 612 may include aligning an outer edge of the fluid management layers. The fluid management layers may be joined by bonding (e.g., welding, heat bonding, etc.) the first plurality of extension pieces to the second plurality of extension pieces. A contact area between the extension pieces may form an optically transparent window.

The method 600 includes placing the fluid management core onto the patient interface layer 614. Operation 614 may include centering the fluid management core above the patient interface layer. Operation 614 may include aligning the fluid communication point with the opening on the patient interface layer. Operation 614 may include coupling (e.g., bonding using a suitable adhesive, etc.) a second, wound-facing side of the fluid management core to the patient interface layer. The patient interface layer may at least partially seal the back side of second fluid management layer (e.g., the second side of the fluid management core) so as to prevent fluid from entering depressions formed into the second side by the second plurality of extensions.

The method 600 further includes placing the barrier layer onto the fluid management core 616. Operation 616 may include centering an aperture of the barrier layer over the fluid management core. Operation 616 may include coupling (e.g., bonding using a suitable adhesive, etc.) the barrier layer to both the fluid management core and the patient interface layer. Together, the barrier layer and the patient interface layer may form a joint proximate to an outer perimeter of the fluid management core, thereby preventing fluid from entering or leaving the fluid management core through a side of the fluid management core. In other exemplary embodiments, more or fewer operations may be performed to produce (e.g., make, manufacture, etc.) the dressing.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A dressing comprising:
   a fluid management core having a first side and a second, wound-facing side, the fluid management core comprising an absorbent material and a plurality of windows, the second side comprising a fluid communication port in fluid communication with the absorbent material, wherein the fluid management core further comprises:
      a first fluid management layer comprising a first plurality of extensions, and
      a second fluid management layer comprising a second plurality of extensions, wherein the first plurality of extensions are aligned with and coupled to the second plurality of extensions;
   a barrier layer coupled to the first side of the fluid management core; and
   a patient interface layer coupled to the second side of the fluid management core, wherein the patient interface layer includes an opening, and wherein the opening is configured to receive fluid from a wound.

2. The dressing of claim 1, wherein each window of the plurality of windows is optically transparent or translucent, and configured to provide at least partial visibility through the fluid management core.

3. The dressing of claim 1,
   wherein the absorbent material is sandwiched between the first fluid management layer and the second fluid management layer.

4. The dressing of claim 1, wherein the first plurality of extensions extend toward the second fluid management layer.

5. The dressing of claim 1, wherein the first plurality of extensions comprises a plurality of geodesic structures.

6. The dressing of claim 1, wherein the fluid communication port comprises a fenestration configured to receive fluid from the opening in the patient interface layer.

7. The dressing of claim 1, wherein the barrier layer comprises an aperture, and wherein the aperture is centered over the first fluid management layer.

8. The dressing of claim 1, wherein the fluid management core is centered over the patient interface layer, and wherein the barrier layer is coupled to the patient interface layer.

9. The dressing of claim 1, further comprising a wicking layer sandwiched between the fluid management core and the patient interface layer, wherein the wicking layer comprises a plurality of perforations, and wherein at least one of the perforations is aligned with one of the windows.

10. A dressing, comprising:
    a barrier layer;
    a first fluid management layer coupled to the barrier layer, the first fluid management layer comprising a first plurality of extensions;
    a second fluid management layer coupled to the first plurality of extensions to define a plurality of optically transparent or translucent windows, and a cavity formed around the coupled extensions and between the first fluid management layer and the second fluid management layer, and wherein one of the fluid management layers comprises a fluid communication port in fluid communication with the cavity;
    an absorbent layer disposed in the cavity; and
    a patient interface layer coupled to one of the first fluid management layer and the second fluid management layer, the patient interface layer comprising an opening, wherein the opening is at least partially aligned with the fluid communication port.

11. The dressing of claim 10, wherein the second fluid management layer comprises a second plurality of extensions, and wherein the first plurality of extensions is coupled to the second plurality of extensions.

12. The dressing of claim 11, wherein the first fluid management layer and the second fluid management layer are identical except for the fluid communication port.

13. The dressing of claim 10, wherein the first plurality of extensions comprises a plurality of geodesic structures.

14. The dressing of claim 10, wherein a portion of each extension of the first plurality of extensions and the second fluid management layer forms a window having a diameter within a range between approximately 3 mm and 15 mm.

15. The dressing of claim 10, wherein the fluid communication port comprises a fenestration in the second fluid management layer.

16. The dressing of claim 10, wherein the barrier layer comprises an aperture, and wherein the aperture is centered over the first fluid management layer.

17. The dressing of claim 10, wherein the fluid management layers are centered over the patient interface layer, wherein the barrier layer is coupled to the patient interface layer.

18. The dressing of claim 10, further comprising a wicking layer sandwiched between the patient interface layer and one of the fluid management layers, wherein the wicking layer comprises a plurality of perforations, and wherein at least one of the perforations is aligned with an extension from the first plurality of extensions.

19. The dressing of claim 10, further comprising a fluid removal port disposed in one of the fluid management layers, wherein the fluid removal port is configured to allow fluid to be removed from the absorbent layer.

20. A method of making a dressing, comprising:
   providing a barrier layer;
   providing a first fluid management layer, the first fluid management layer comprising a first plurality of extensions;
   providing a second fluid management layer comprising a second plurality of extensions, wherein one of the fluid management layers comprises a fluid communication port;
   providing a patient interface layer comprising an opening;
   placing an absorbent layer onto one of the first fluid management layer and the second fluid management layer;
   joining the first fluid management layer and the second fluid management layer, wherein the absorbent layer is in fluid communication with the fluid communication port and disposed in between the first fluid management layer and the second fluid management layer to define a fluid management core;
   aligning and coupling the first plurality of extensions with the second plurality of extensions to form a plurality of optically transparent or translucent windows;
   placing the fluid management core onto the patient interface layer; and
   placing the barrier layer onto the fluid management core opposite the patient interface layer.

21. The method of claim 20, further comprising aligning the opening with the fluid communication port.

22. The method of claim 20, further comprising printing the absorbent layer onto one of the fluid management layers.

23. The method of claim 20, further comprising bonding the fluid management core to the patient interface layer and the barrier layer.

\* \* \* \* \*